(12) United States Patent
Rennó

(10) Patent No.: US 10,336,465 B2
(45) Date of Patent: Jul. 2, 2019

(54) ICE CRYSTALS AND VOLCANIC ASH DETECTION SYSTEM

(71) Applicant: THE REGENTS OF THE UNIVERSITY OF MICHIGAN, Ann Arbor, MI (US)

(72) Inventor: Nilton O. Rennó, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 214 days.

(21) Appl. No.: 15/399,088

(22) Filed: Jan. 5, 2017

(65) Prior Publication Data
US 2017/0197728 A1   Jul. 13, 2017

Related U.S. Application Data (60) Provisional application No. 62/276,287, filed on Jan. 8, 2016.

(51) Int. Cl.
*B64D 45/00* (2006.01)
*B64D 15/22* (2006.01)
(Continued)

(52) U.S. Cl.
CPC ............. *B64D 45/00* (2013.01); *B64D 15/20* (2013.01); *B64D 15/22* (2013.01); *B64D 43/00* (2013.01);
(Continued)

(58) Field of Classification Search
CPC .................................................. B64D 45/00
(Continued)

(56) References Cited

U.S. PATENT DOCUMENTS 3,767,915 A * 10/1973 Battist ..................... G01T 1/178
250/366
3,970,428 A * 7/1976 Barringer ............... G01V 5/025
73/863.22
(Continued)

FOREIGN PATENT DOCUMENTS

EP      0537206 B1    1/1996
EP      1401707 A1    3/2004
(Continued)

OTHER PUBLICATIONS

International Search Report and Written Opinion of the International Searching Authority dated Apr. 21, 2017 regarding PCT/US2017/012410.

(Continued)

*Primary Examiner* — Tarifur R Chowdhury
*Assistant Examiner* — Omar H Nixon
(74) *Attorney, Agent, or Firm* — Harness, Dickey & Pierce, P.L.C.

(57) ABSTRACT

Methods and systems for detecting ice crystals and volcanic ash in concentrations capable of causing power loss in aircraft jet engines. These hazard conditions are inferred from the detection of ice crystals or ash in air recently lifted from the lower atmosphere by convective updrafts. The detection systems can comprise subsystems for detecting air recently lifted from the lower troposphere by measuring radon activity along the aircrafts' flight track, as well as subsystems for detecting ice crystals or volcanic ash around the aircraft via multispectral measurements. The detection of ice crystals in air recently lifted from the lower troposphere indicates that the ice crystals are likely present in large concentration. The detection of volcanic ash in air recently lifted from lower atmosphere also indicates that volcanic ash is likely present in high concentration. These are hazards (Continued)

conditions that could cause power loss, jet engine flameout, and even damage jet engines.

9 Claims, 5 Drawing Sheets

(51) Int. Cl.
| | |
|---|---|
| G01N 21/35 | (2014.01) |
| G01N 33/00 | (2006.01) |
| G01V 8/12 | (2006.01) |
| B64D 15/20 | (2006.01) |
| B64D 43/00 | (2006.01) |
| G01V 9/00 | (2006.01) |
| G01N 21/17 | (2006.01) |

(52) U.S. Cl.
CPC ......... *G01N 21/35* (2013.01); *G01N 33/0036* (2013.01); *G01V 8/12* (2013.01); *G01N 2021/1793* (2013.01); *G01N 2201/12* (2013.01); *G01V 9/007* (2013.01); *Y02A 50/25* (2018.01)

(58) Field of Classification Search
USPC ......................................................... 356/432
See application file for complete search history.

(56) References Cited

U.S. PATENT DOCUMENTS

| | | | |
|---|---|---|---|
| 4,054,255 A | 10/1977 | Magenheim | |
| 4,221,482 A * | 9/1980 | Macourt | G01N 21/73 |
| | | | 250/DIG. 2 |
| 4,274,091 A | 6/1981 | Decker | |
| 4,441,363 A | 4/1984 | Hill et al. | |
| 4,463,252 A | 7/1984 | Brennan et al. | |
| 4,804,849 A | 2/1989 | Booth et al. | |
| 4,809,197 A | 2/1989 | Tashiro et al. | |
| 4,819,480 A | 4/1989 | Sabin | |
| 4,920,263 A * | 4/1990 | Fimian | G01T 1/003 |
| | | | 250/253 |
| 4,965,573 A | 10/1990 | Gallagher et al. | |
| 4,984,163 A | 1/1991 | Kuwana et al. | |
| 5,005,015 A | 4/1991 | Dehn et al. | |
| 5,028,929 A | 7/1991 | Sand et al. | |
| 5,035,472 A | 7/1991 | Hansen | |
| 5,124,914 A * | 6/1992 | Grangeat | A61B 6/4447 |
| | | | 378/50 |
| 5,218,206 A | 6/1993 | Schmitt et al. | |
| 5,301,905 A | 4/1994 | Blaha | |
| 5,313,202 A | 5/1994 | Hansman, Jr. et al. | |
| 5,497,100 A | 3/1996 | Reiser et al. | |
| 5,521,594 A | 5/1996 | Fukushima | |
| 5,596,320 A | 1/1997 | Barnes | |
| 5,695,155 A | 12/1997 | Macdonald et al. | |
| 5,796,344 A | 8/1998 | Mann et al. | |
| 5,818,339 A | 10/1998 | Giles | |
| 5,905,570 A | 5/1999 | White et al. | |
| 6,040,916 A | 3/2000 | Griesinger | |
| 6,091,335 A | 7/2000 | Breda et al. | |
| 6,161,075 A | 12/2000 | Cohen | |
| 6,166,645 A | 12/2000 | Blaney | |
| 6,166,657 A | 12/2000 | Mann | |
| 6,269,320 B1 | 7/2001 | Otto | |
| 6,384,611 B1 | 5/2002 | Wallace et al. | |
| 6,430,996 B1 | 8/2002 | Anderson et al. | |
| 6,459,083 B1 | 10/2002 | Finkele et al. | |
| 6,819,265 B2 | 11/2004 | Jamieson et al. | |
| 6,921,898 B1 | 7/2005 | Chen | |
| 6,977,597 B2 | 12/2005 | Doherty | |
| 7,100,427 B2 | 9/2006 | Kahn et al. | |
| 7,104,502 B2 | 9/2006 | Otto et al. | |
| 7,119,891 B2 | 10/2006 | White et al. | |
| 7,224,453 B2 | 5/2007 | Elman | |
| 7,265,846 B2 | 9/2007 | Forsyth | |
| 7,301,478 B1 | 11/2007 | Chinn et al. | |
| 7,370,525 B1 | 5/2008 | Zhao et al. | |
| 7,424,399 B2 | 9/2008 | Kahn et al. | |
| 7,796,833 B2 | 9/2010 | Polonskiy et al. | |
| 7,839,301 B2 | 11/2010 | Doherty et al. | |
| 7,986,408 B2 | 7/2011 | Ray et al. | |
| 8,000,847 B2 | 8/2011 | Shue | |
| 8,044,823 B2 | 10/2011 | Doherty et al. | |
| 8,325,338 B1 | 12/2012 | Pope et al. | |
| 8,350,910 B2 | 1/2013 | Capello et al. | |
| 8,666,570 B1 * | 3/2014 | Tillotson | G06T 7/0008 |
| | | | 340/945 |
| 8,711,008 B2 | 4/2014 | Cook et al. | |
| 8,796,627 B2 | 8/2014 | Rockwell et al. | |
| 8,854,464 B2 | 10/2014 | Ishi et al. | |
| 9,013,332 B2 | 4/2015 | Meis | |
| 9,041,926 B2 | 5/2015 | Ray et al. | |
| 9,297,755 B2 | 3/2016 | Renno | |
| 9,302,777 B2 | 4/2016 | Renno | |
| 9,304,081 B2 | 4/2016 | Renno | |
| 9,305,220 B2 | 4/2016 | Funayama et al. | |
| 2002/0162962 A1 | 11/2002 | Rudolph | |
| 2003/0150992 A1 | 8/2003 | Chavez et al. | |
| 2003/0169186 A1 | 9/2003 | Vopat | |
| 2004/0036630 A1 | 2/2004 | Jamieson et al. | |
| 2004/0206854 A1 | 10/2004 | Shah et al. | |
| 2004/0231410 A1 | 11/2004 | Bernard et al. | |
| 2005/0002435 A1 | 1/2005 | Hashimoto et al. | |
| 2005/0100336 A1 | 5/2005 | Mendenhall et al. | |
| 2005/0105103 A1 | 5/2005 | Schietinger et al. | |
| 2005/0151965 A1 | 7/2005 | Bissett et al. | |
| 2005/0167593 A1 | 8/2005 | Forsyth | |
| 2005/0218268 A1 | 10/2005 | Otto et al. | |
| 2005/0230553 A1 | 10/2005 | Otto et al. | |
| 2006/0050270 A1 | 3/2006 | Elman | |
| 2006/0261975 A1 | 11/2006 | Fridthjof | |
| 2007/0074415 A1 | 4/2007 | Gagnon | |
| 2008/0110254 A1 | 5/2008 | Zhao et al. | |
| 2008/0129541 A1 | 6/2008 | Lu et al. | |
| 2008/0161878 A1 | 7/2008 | Tehrani et al. | |
| 2008/0218385 A1 | 9/2008 | Cook et al. | |
| 2009/0222238 A1 | 9/2009 | Gagnon | |
| 2009/0261811 A1 | 10/2009 | Gordon | |
| 2010/0072367 A1 | 3/2010 | Meurer | |
| 2010/0085175 A1 | 4/2010 | Fridthjof | |
| 2010/0110431 A1 | 5/2010 | Ray et al. | |
| 2010/0131203 A1 | 5/2010 | Lilie et al. | |
| 2011/0019188 A1 | 1/2011 | Ray et al. | |
| 2011/0135197 A1 | 6/2011 | Paris et al. | |
| 2011/0213554 A1 * | 9/2011 | Archibald | G01V 9/007 |
| | | | 702/6 |
| 2012/0085868 A1 | 4/2012 | Barnes | |
| 2012/0123637 A1 | 5/2012 | Funayama et al. | |
| 2012/0140233 A1 | 6/2012 | Rockwell et al. | |
| 2012/0182544 A1 * | 7/2012 | Asahara | G01S 7/499 |
| | | | 356/73 |
| 2012/0187301 A1 * | 7/2012 | Markson | G01T 1/178 |
| | | | 250/362 |
| 2012/0191350 A1 | 7/2012 | Prata et al. | |
| 2012/0193477 A1 * | 8/2012 | Thorez | B64D 15/20 |
| | | | 244/134 F |
| 2012/0266669 A1 | 10/2012 | Sage | |
| 2012/0274938 A1 | 11/2012 | Ray | |
| 2012/0327410 A1 | 12/2012 | Maston | |
| 2013/0008174 A1 | 1/2013 | Gould et al. | |
| 2013/0234884 A1 * | 9/2013 | Bunch | G01W 1/00 |
| | | | 342/26 B |
| 2013/0249701 A1 | 9/2013 | Zhang | |
| 2014/0112537 A1 | 4/2014 | Frank et al. | |
| 2014/0347189 A1 | 11/2014 | Weksler et al. | |
| 2014/0372069 A1 | 12/2014 | Nuzzio | |
| 2015/0019185 A1 | 1/2015 | Cunningham et al. | |
| 2015/0120092 A1 * | 4/2015 | Renno | B64D 15/20 |
| | | | 701/3 |

(56) References Cited

U.S. PATENT DOCUMENTS

| | | | |
|---|---|---|---|
| 2015/0120093 | A1 | 4/2015 | Renno |
| 2015/0170485 | A1 | 6/2015 | DeCusatis et al. |
| 2017/0197728 | A1 | 7/2017 | Renno |

FOREIGN PATENT DOCUMENTS

| | | |
|---|---|---|
| EP | 2637045 A2 | 9/2013 |
| JP | 2001-099710 A | 4/2001 |
| JP | 2006046936 A | 2/2006 |
| JP | 2009115498 A | 5/2009 |
| JP | 4492883 B2 | 6/2010 |
| WO | 2014132073 A1 | 9/2014 |
| WO | 2015116873 A2 | 8/2015 |
| WO | 2016000666 A1 | 1/2016 |

OTHER PUBLICATIONS

Zahorowski et al., Vertical Radon-222 Profiles in the Atmospheric Boundary Layer, CAWCR 5th Annual Workshop, Atmospheric Composition Observations and Modelling and the Cape Grim Annual Science Meeting, Nov. 15-17, 2011, Bureau of Meteorology, Melbourne, Australia.
Turekian et al., Geochemistry of Atmospheric Radon and Radon Products, Annual Review of Earth and Planetary Sciences, 1977, vol. 5, pp. 227-255.
Jacob and Prather, Radon-222 as a Test of Convective Transport in a General Circulation Model, Tellus (1990), 42B, pp. 118-134.
Mason, Engine Power Loss in Ice Crystal Conditions, Aero Quarterly, 2007.
Guffanti et al., Encounters of Aircraft with Volcanic Ash Clouds: a Compilation of Known Incidents, 1953-2009, U.S. Department of the Interior, U.S. Geological Survey, Data Series 545, Version 1.0, 2010, Reston, Virginia, U.S.A.
Li et. al., A Three-Dimensional Global Episodic Tracer Transport Model: 1. Evaluation of its Transport Processes by Radon 222 Simulations, Journal of Geophysical Research, vol. 101, No. D20, pp. 25,931-25,947, Nov. 20, 1996.
Kritz et al., Radon Measurements in the Lower Tropical Stratosphere: Evidence for Rapid Vertical Transport and Dehydration of Tropospheric Air, Journal of Geophysical Research, vol. 98, No. D5, pp. 8725-8736, May 20, 1993.
Lambert et al., Volcanic Output of Long-Lived Radon Daughters, Journal of Geophysical Research, vol. 87, No. C13, pp, 11,103-11,108, Dec. 20, 1982.
Schery, An Estimate of the Global Distribution of Radon Emissions from the Ocean, Geophysical Research Letters, vol. 31, Oct. 7, 2004.
Williams et al., The Vertical Distribution of Radon in Clear and Cloudy Daytime Terrestial Boundary Layers, Journey of Atmospheric Sciences, vol. 68, pp. 155-174, Jan. 2011.
Moore et al., 222Rn, 210 Pb, 210Bi, and 210Po Profiles and Aerosol Residence Times Versus Altitude, Journal of Geophysical Research, vol. 78, No. 30, Oct. 20, 1973.
Martins et. al., Remote Sensing the Vertical Profile of Cloud Droplet Effective Radius, Thermodynamic Phase, and Temperature, Atmospheric Chemistry and Physics Discussions, 7, 4481-4519, 2007.
Kou, L., Labrie, D., and Chylek, P., "Refractive indices of water and ice in the 0.65- to 2.5 µm spectral range", (Jul. 1993), Appl. Opt., 32(19), 3531-3540.
Vanderlei Martins, J., et al., "Remote sensing the vertical profile of cloud droplet effective radius, thermodynamic phase, and temperature", (Mar. 2007), Atmos. Chem. Phys. Discuss., 7, 4481-4519.
Rennó, N. O., et al., "CHASER: An Innovative Satellite Mission Concept to Measure the Effects of Aerosols on Clouds and Climate", (May 2013), Bull. Amer. Meteor. Soc., 94, 685-694.
International Search Report and Written Opinion, International Application No. PCT/US2014/038003, dated Aug. 14, 2014, 13 pages.
International Search Report and Written Opinion, International Application No. PCT/US2014/047415, dated Nov. 20, 2014, 12 pages.
Kendra, J. R., Ulaby, F. T., & Sarabandi, K. (1994). Snow probe for in situ determination of wetness and density. Geoscience and Remote Sensing, IEEE Transactions on Geoscience and Remote Sensing, 32 (6), 1152-1159.
Sarabandi, K., & Li, E. S. (1997). Microstrip ring resonator for soil moisture measurements. Geoscience and Remote Sensing, IEEE Transactions on Geoscience and Remote Sensing, 35 (5), 1223-1231.
Dionigi, M., Ocera, A., Fratticcioli, E., and Sorrentino, R. (2004), A new resonant probe for Dielectric permittivity measurement, European Micro. Conf. Dig., Amsterdam, 673-676.
Fratticcioli, E., M. Dionigi, and R. Sorrentino (2004), "A simple and low-cost measurement system for the complex permittivity characterization of materials," IEEE Trans. on Instrumentation and Measurement, 53(4), 1071-1077.
Sagnard, F. and Y.-L. Beck (2009), "Experimental study of the influence of moisture and dry density on a silt soil using a monopole probe," Micro and Optical Tech. Lett., 51(3), 820-826.
Chang, K., & Hsieh, L. H. (2004), Microwave Ring Circuits and Related Structures, Second Edition, John Wiley & Sons, Inc.
International Search Report and Written Opinion, International Application No. PCT/US2014/061949, dated Feb. 9, 2015, 9 pages.
Nakauchi, S., K Nishino, T. Yamashita, "Selection of Optimal Combinations of Band-Pass Filters for Ice Detection by Hyperspectral Imaging," Opt. Express 20, 986-1000 (2012).
Gregoris, D., S. Yu, and F. Teti, "Multispectral Imaging of Ice," Paper Presented at the Canadian Conference on Electrical nd Computer Engineering, 4, 2051-2056.
Jonsson, P, Remote Sensor for Winter Road Surface Status Detection. In: Proceedings of IEEE Sensors (2011) p. 1285-8.

\* cited by examiner

ICE CRYSTALS AND VOLCANIC ASH DETECTION SYSTEM

CROSS-REFERENCE TO RELATED APPLICATIONS

This application claims the benefit of U.S. Provisional Application No. 62/276,287, filed on Jan. 8, 2016. The entire disclosure of the above application is incorporated herein by reference.

GOVERNMENT INTEREST

This invention was made with government support under grant AGS1118467 awarded by the National Science Foundation. The Government has certain rights in the invention.

FIELD

The present disclosure is for methods, systems, and apparatuses capable of detecting ice crystals and volcanic ash in large concentrations in air recently lifted from the lower troposphere by convective updrafts in thunderstorms or volcanic plumes.

BACKGROUND AND SUMMARY

This section provides background information related to the present disclosure which is not necessarily prior art. It further provides a general summary of the disclosure, but not a comprehensive disclosure of its full scope or all of its features.

Generally, ice crystals and volcanic ash in large concentrations are hazards to aviation as they can lead to damage, power loss, and flameout in jet engines.

In fact, ice crystals icing has caused hundreds of jet engine power loss events in the past 30 years (e.g., Mason, 2007). Most of these events occurred in conditions that appear benign to an alert pilot. Moreover, they occurred well above the altitudes where the supercooled water droplets that cause the more common aircraft airframe icing exist. Power loss is defined as engine instability, such as a surge, stall, or flameout (engine shutdown), that results in extremely low power values. Small ice crystals in large concentrations cause these hazard events.

Volcanic ash can cause power loss and even damage jet engines while an airplane is flying in conditions that also appear benign to an alert pilot, in particular during night flights. Volcanic ash has caused a significant number of airplane incidents and air traffic disruptions in the past 30 years (e.g., Guffanti et al., 2010). This includes the shutdown of all four engines of a Boeing 747 without the pilots knowing its cause because of lack of awareness that they were flying in volcanic ash. The eruption of Iceland's Eyjafjallajökull Volcano in 2010 produced an ash plume that caused a weeklong closure of the airspace above Europe and the North Atlantic. The detection of volcanic ash could help pilots mitigate these problems.

Aircraft on-board weather radars are capable of detecting large particles, such as hail, rain, and snow, but not volcanic ash or the small ice crystals found in high concentrations near thunderstorms. Unfortunately, volcanic ash and small ice crystals are a major cause of jet engine power loss and flameout. Hazard ice crystals icing conditions can be inferred by detecting the presence of ice crystals in air recently lifted from the lower troposphere by thunderstorms updrafts. Hazard volcanic ash conditions can be inferred by detecting the presence of volcanic ash in air recently lifted from the lower troposphere by convective updrafts in volcanic plumes.

Radon-222 (radon) is a naturally occurring radioactive noble gas of terrestrial origin commonly used as atmospheric tracer (e.g., Zahorowski et al. 2004). Radon is produced by the decay of long-lived radium-226 present in rocks and soils. Radon is a good atmospheric tracer because by being a noble gas it does not react with any atmospheric constituent. Being inert and poorly soluble in water (Jacob and Prather 1990; Li and Chang 1996), radon is not removed by wet atmospheric removal processes such as rainfall. Indeed, the only significant atmospheric sink of radon is radioactive decay with a half-life time-scale of 3.82 days. Thus, vertical transport processes, such as convective updrafts in thunderstorms and in volcanic plumes, cause significant increases in radon activity in the upper atmosphere. In fact, measurements by NASA high-altitude research aircrafts demonstrate that radon can be used to identify air recently transported by thunderstorm updrafts even at altitudes above 15 km (e.g., Kritz et al., 1993).

Radon (radon-222) activity can be determined by measuring the radioactivity of radon and/or its decay products. Since radon has a half-life of 3.82 days, a particular radon nucleus may decay at any time but is most likely to decay in about 8 days (two half-lives). When a radon nucleus decays, it emits an alpha particle with 5.49 MeV of energy while the nucleus transforms into polonium-218. Polonium is a metal and therefore it sticks to things it contacts, such as aerosols, cloud particles and the surfaces of an instrument. Polonium-218 nuclei have a half-life of 3.05 minutes, which means that it is most likely to decay in about 6 minutes. Like radon, polonium-218 emits an alpha particle when it decays, but with energy of 6.00 MeV instead of radon's 5.49 MeV.

The detection of alpha radiation with solid-state detectors is frequently used for continuous measurements of radon activity. Solid-state alpha detectors are semiconductors (e.g. silicon) that convert alpha radiation directly into an electrical signal. This allows the energy of each alpha particle to be measured, making possible to determine which isotope (e.g., radon-222, polonium-218, polonium-214) produced it. Continuous measurement of radon requires instruments with low background noise, fast response, and fast recovery after exposure to high radon levels. Counting the alpha particles emitted by the decay of polonium-218 and ignoring the alpha particles emitted by the decay of polonium-214 that accumulates in the instrument, allows measurements with response of less than 10 minutes even for an instrument with sub-liter measurement chamber.

The concentrations of radionuclides, such as radon-222 (radon), are usually expressed in terms of disintegrations per unit time, defined as activity $A=N\lambda$, where N is the number of radionuclide atoms, and $\lambda$ is the atom radioactive decay constant. Common units of activity are disintegrations per minute (dpm), pico ($10^{-12}$) Curie (pCi), and Becquerels (Bq); 1 Bq=60 dpm, and 1 pCi=2.2 dpm.

The flux of radon from the ground into the atmosphere is about $10^4$ atoms/$m^2$-s. Over the open oceans, the emission of radon is two to three orders of magnitude smaller than over land (Turekian et al. 1977; Lambert et al. 1982; Schery and Huang 2004), but radon activity over the open oceans is still orders of magnitude larger than kilometers above the surface (Kritz et al., 1993; Williams et al., 2011). Since the radon has a half-life of 3.82 days, it is not transported efficiently from the surface into the upper atmosphere by diffusion. Thus, radon activity in the upper troposphere and stratosphere is an excellent indicator of fast and recent transport by convective updrafts.

Radon activities in the upper troposphere and stratosphere, where jet aircrafts typically cruise are usually less than 0.5 pCi/scm (e.g., Moore at al., 1973), where scm is a standard cubic meter. In contrast, near the surface where convective updrafts originate radon activity is orders of magnitude larger than in the upper troposphere and in the stratosphere. Indeed, radon activity varies from more than about 5-10 pCi/scm over the oceans to more than 100 pCi/scm over land. Updrafts in thunderstorms and volcanic plumes transport radon rich near-surface air upwards because by being poorly soluble in water (e.g., clouds and precipitation) the radon concentration does not decrease significantly in storm updrafts and by being a noble gas radon does not react with atmospheric constituents.

Measurements by high-altitude aircrafts indicate that tropospheric air injected into the stratosphere by convective updrafts have mean radon activity of about 20 pCi/scm, an order of magnitude larger than the value observed in the upper troposphere (Kritz et al., 1993). Moreover, measurements inside and just above cirrus anvils indicate radon activity of the order of 10 pCi/scm, a significantly elevated value with respect to the background level of less than 0.5 pCi/scm at the same level (Kritz et al., 1993). Thus, elevated radon activity would be a good indicator that a cirrus cloud was formed in air recently originating in the lower atmosphere and therefore with large water content. Similarly large radon activity is expected in ash clouds because ash is lifted by updrafts originating at the surface where radon activity is high (of the order of 100 pCi/scm).

The aircraft hazards detection system of the present invention comprises a subsystem capable of detecting ice crystals and volcanic ash, as well as a radon activity sensor such as an alpha particle detector capable of identifying the presence of air recently lifted from the lower troposphere. The detection of ice crystals or volcanic ash in air recently lifted from the lower troposphere indicates a potentially hazards condition that can cause power loss and even damage jet engines.

Unfortunately, few systems exist that are capable of reliably detecting small ice crystals or volcanic ash, and providing an associated alert. Prior art approaches for detecting ice crystals include a variety of optical method. For example, U.S. Pat. No. 7,986,408B2 refers to a device for detecting and distinguishing airborne liquid water droplets from ice crystals by illuminating the target with a circularly polarized light beam and detecting changes in the light polarization. The backscattered light received by the device is converted into two linearly polarized components. These two components are then used to calculate parameters indicative of the presence or absence of airborne ice crystals and water droplets.

U.S. Pat. No. 6,819,265 refers to an ice detection system for monitoring the airspace ahead of the aircraft. The system comprises optical elements designed to direct pulsed laser beams into the airspace ahead of an aircraft. Another set of optical elements is used to receive the backscattered light and separate it into multiple wavelengths. Signals of the light detected at various pre-determined wavelengths are used to determine if airspace conditions ahead of the aircraft is likely to cause ice accretion on the surface of the aircraft.

U.S. Pat. No. 7,370,525 refers to a dual channel system for detecting ice accretion on aircraft surfaces. The system illuminates the surface of the aircraft with linearly polarized light. Optical systems with polarization sensitivity aligned to the transmitted light, and with polarization sensitivity orthogonal to it, are used to acquire the backscattered light. The ratio of the intensities of the light signals is used to determine the presence or absence of ice.

U.S. Pat. No. 6,269,320 refers to an in-situ Supercooled Large Droplet (SLD) detector. This system takes advantage of boundary layer flow patterns to detect SLD. It is capable of distinguishing between the presence of water droplets that cause regular cloud icing and SLD icing. This system detects ice after it accumulates on aircrafts surfaces, it does not provide warnings when a hazards situation occurs in the airspace ahead of an aircraft.

U.S. Pat. No. 6,091,335 refers to an optical device for detecting icing conditions outside the boundary layer of the aircraft. The device employs change in light polarization for detecting icing conditions. It includes a light source to illuminate an external measurement volume. Light backscattered by the water droplets in an external volume is measured using photodetectors. Analysis of the polarization of the light collected is used to estimate the severity of the icing conditions.

Prior art approaches for detecting volcanic ash also include methods for detecting changes in the polarization light emitted towards the target. For example, U.S. Pat. No. 9,041,926B2 refers to a method for determining the presence of volcanic ash within a cloud by analyzing changes in the polarization of light used to illuminate it. A circularly polarized light is used to illuminate the airspace ahead of an aircraft. Analysis of the backscattered light is used to determine the presence of volcanic ash within the cloud. This analysis includes the determination of the degree to which the polarization changes.

According to the principles of the present teachings, an ice crystals and volcanic ash detection system is provided that overcomes the disadvantages of the prior art and is particularly useful in detecting hazardous conditions invisible even to the most alert pilots. In most embodiments of the present teachings, the system detects ice crystals and volcanic ash recently lifted by measuring radon activity and making multi-spectral measurements of radiance.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Figure 6:
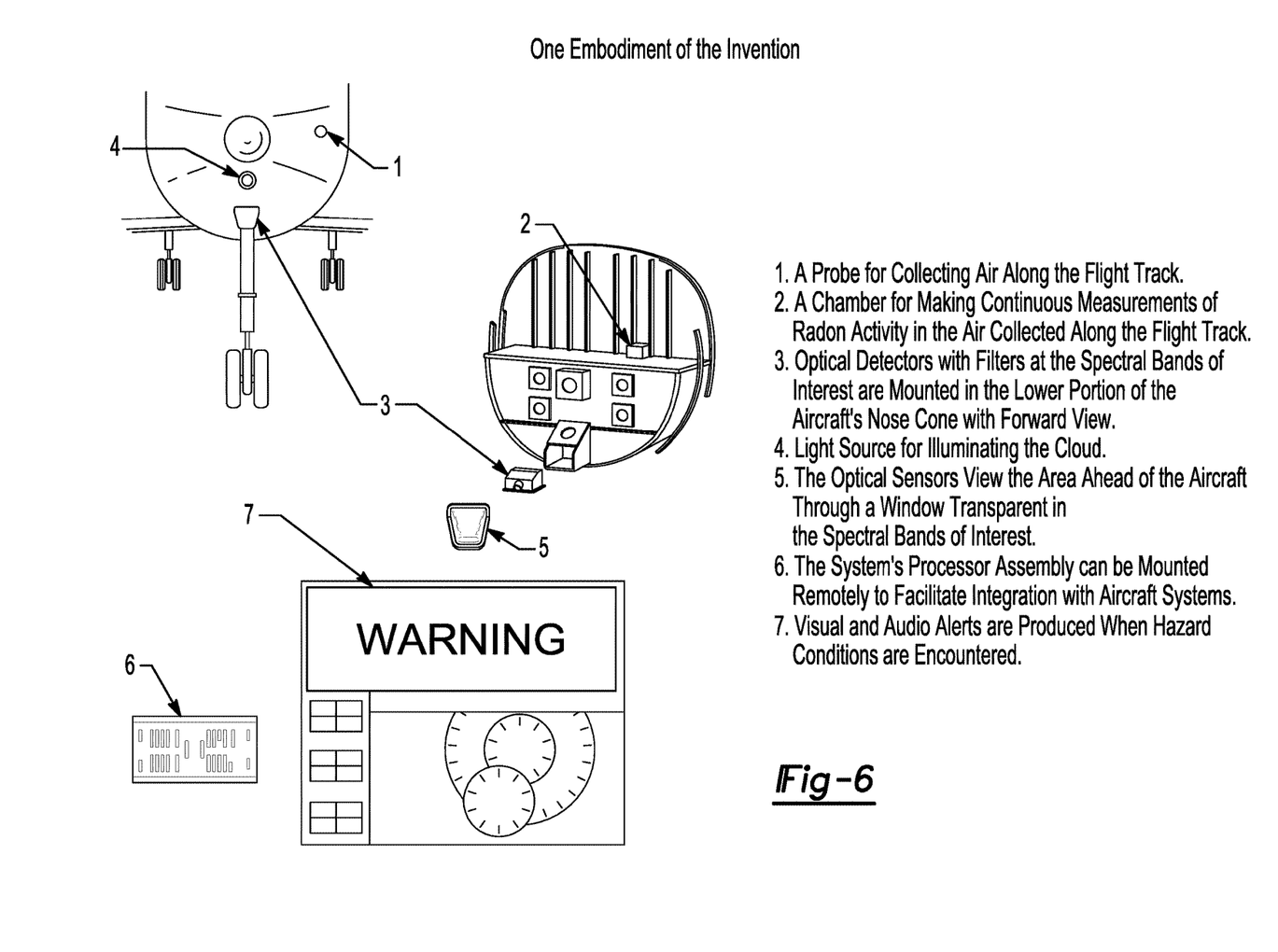
FIG. 6 is a sketch of one possible embodiment of the hazards detection system of this invention.

According to the principles of the present teachings, an ice crystals and volcanic ash detection system is provided (see at least FIG. 6) having a probe 1 for collecting air samples along the flight track, at least one chamber for measuring radon activity 2 in the air samples collected, optical sensors for detecting cirrus clouds and volcanic ash 3, if desired a light source for illuminating the target 4, an window transparent in the spectral bands of interest covering the optical detectors 5, a data processing unit 6, and an output system 7. These components will be described in greater detail herein. However, it should be understood that the present teachings provide utility in a wide variety of applications. More particularly, and without limitation, the present teachings are well suited for use in detecting ice crystals and volcanic ash from a variety of airborne platforms. Moreover, the present teachings can be incorporated into a number of airborne vehicles such as airplanes, unmanned air vehicles (UAVs), balloons, and blimps. It should be understood that the system could also be used for monitoring at fixed locations.

It should further be understood that the present teachings can be incorporated into a number of subsystems of airborne-based vehicles, such as, but not limited to, aircraft engines, turbines, propellers, blades, air intakes, control surfaces, wings, stabilizers, and other components of aircraft; helicopters; UAVs; blimps; balloons (e.g. weather balloons); and other objects of interest.

In all applications, the particular mounting location of the radon detector and optical sensor, including its orientation are not necessarily crucial, so long as detection performance is maintained. Therefore, the present teachings should not be regarded as being limited to any one particular mounting specification.

Fundamental Principles

At the outset, it is important to understand various fundamental principles that are employed as part of the present teachings. To this end, it should be understood that radon activity is an excellent indicator of air transported from near the surface into the upper troposphere or stratosphere by recent convective updrafts because the sources of radon are at the surface, and its half-life is only 3.82 days. Since, radon activity is negligibly small (less than 0.5 pCi/scm) in the undisturbed upper troposphere and stratosphere, any significantly high radon activity (see FIG. 2) is indicative of recent transport by convective updrafts.

Figure 3A:
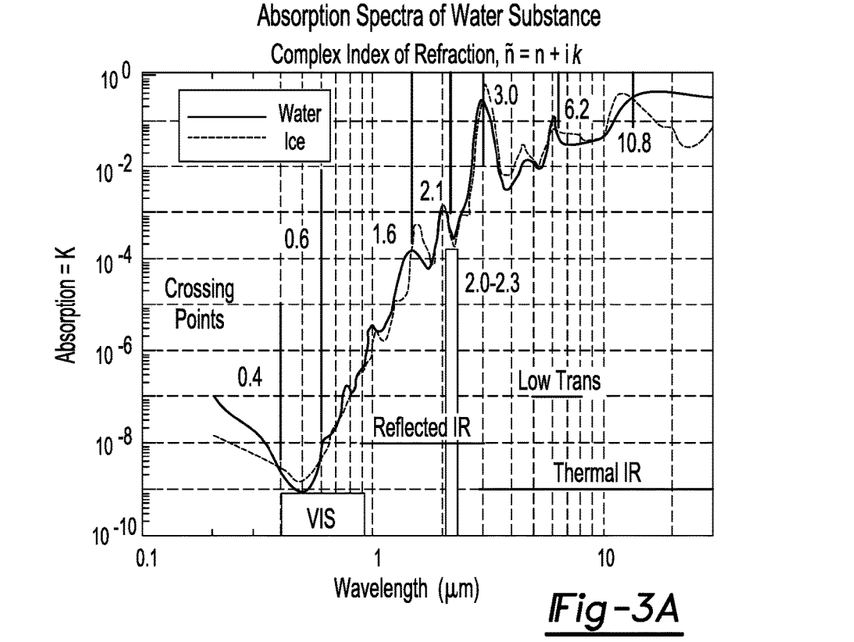
FIG. 3A is a sketch of the absorption of light by water substance showing that liquid water and ice can be detected and distinguished from each other via optical measurements around multiple crossover points.
Figure 3B:
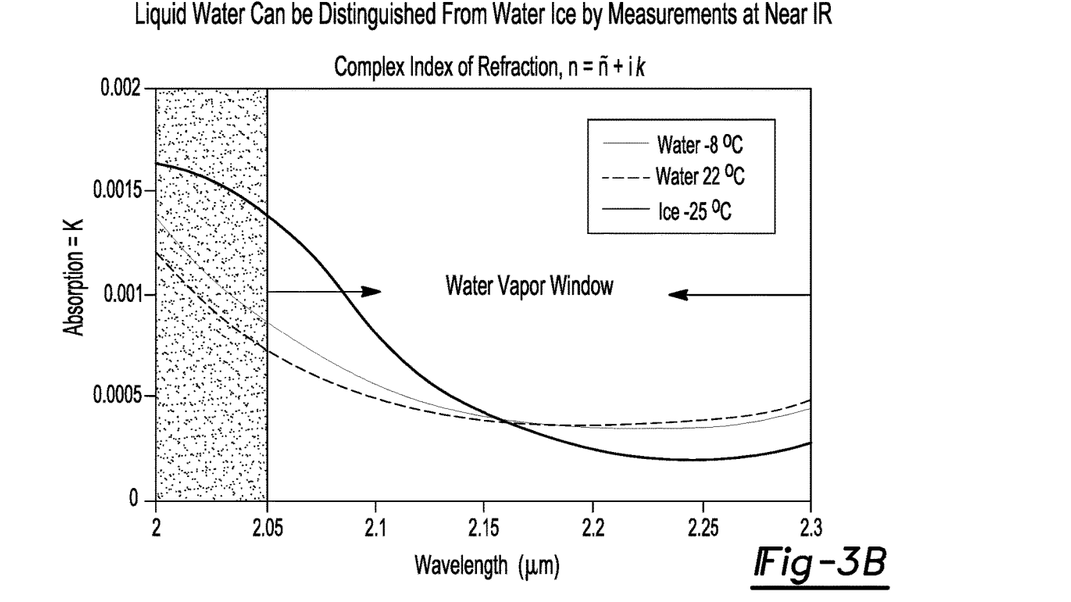
FIG. 3B is a detailed sketch of the absorption of light by water substance around the 2.15 μm crossover point.
Figure 4:
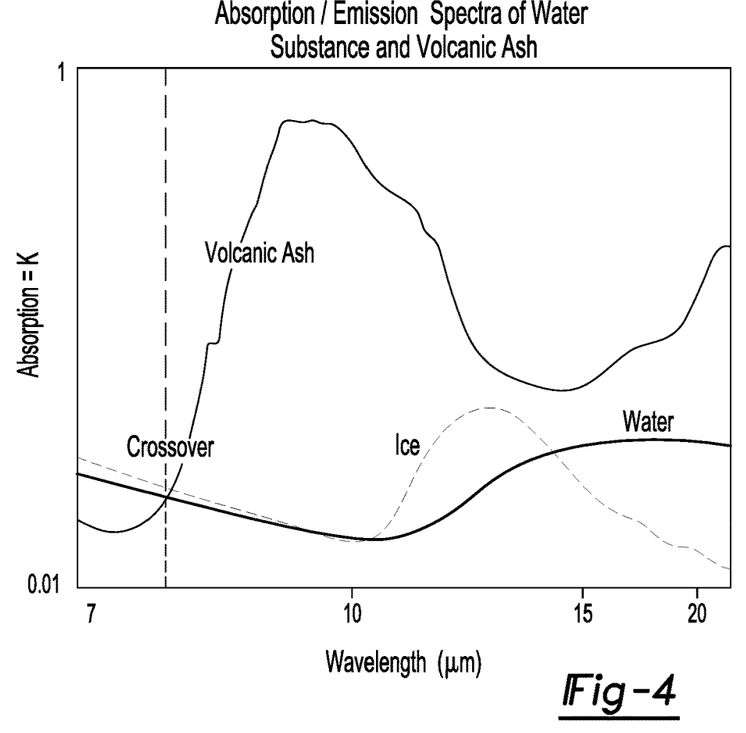
FIG. 4 is a sketch of the absorption of light by liquid water, ice, and volcanic ash. It indicates that infrared absorption spectra of volcanic plumes vary strongly with wavelength between 7 and 12 μm. It also indicates that measurements of radiance around the crossover point at about 8 μm can be used to distinguish ice crystals or water clouds from volcanic ash clouds.

Liquid water and ice exhibit fundamental characteristics when exposed to electromagnetic radiation, in particular at wavelengths of about 0.4, 0.6, 1.5, 2.1, 3.0, 6.2, and 10.8 µm where the curves representing the absorption of electromagnetic radiation by water and ice cross each other as indicated in FIGS. 3A and 3B. Volcanic ash and ice/water exhibit similar fundamental characteristics around 8 µm, as shown in FIG. 4. Measurements of the relative radiance between each side of a crossover point can be used to detect clouds of ice particles and water droplets. Measurements on each side of the crossover point around 8 µm can be used to distinguish ice/water clouds from volcanic ash. The change in relative brightness could be caused by the absorption of electromagnetic radiation impinging on the target (attenuating reflections) as it occurs in the reflected IR and visible portions of the spectrum, or by the emittance of thermal emission as it occurs in the thermal IR portion of the spectrum around 8 (volcanic ash and ice/water) and 10.8 µm (ice and water).

For purposes of the present discussion, spectral bands around crossover points (spectrum range of interest) are used. The ideal spectral bands for the detection of volcanic ash are between about 7 and 10 µm (see FIG. 4). The ideal bands for the detection of ice crystals are between 2.05 and 2.30 µm where absorption and natural illumination during the day is significant, or around 3.0 µm where absorption peaks (see FIGS. 3A and 3B). The 2.05 to 2.30 µm band is used here to exemplify the application of the technique. In this spectral region, 2.05 µm has been determined to be a lower limit due to the fact that the atmosphere tends to absorb a greater portion of the light below 2.05 µm, thereby negatively affecting detection efficiency. However, at wavelengths between about 2.05 and 2.30 µm atmospheric absorption is negligible and the absorption properties of liquid water and ice exhibit predictable characteristics (Kuo et al., 1993; Martins at al., 2007) that allows the easy detection of ice and water as illustrated in FIG. 3B. As discussed below, shortwave infrared (SWIR) at spectral bands between about 2.05 and about 2.15 µm and between about 2.15 and about 2.30 µm can be used to distinguish liquid water droplets from ice particles unambiguously. This range (2.05-2.30 µm) is generally referred to as a 'water vapor window.'

Upon careful review of FIG. 3B, one will note that a transition or crossover occurs at about 2.15 µm where the absorption characteristics of liquid water invert relative to the absorption characteristics of ice. In this way, comparison of the absorption of liquid water and ice in this water vapor window or spectrum range of interest (about 2.05 µm to about 2.30 µm), specifically using measurements of reflectance or radiance obtained from opposing sides of this transition or crossover point (about 2.15 µm), permits one to detect/determine the presence of liquid water or ice unambiguously. Thus, by measuring the radiance/reflectance at wavelengths on opposing sides of this crossover point, one can determine the presence of liquid water or ice based on a ratio of the measured radiance/reflectance. Ideally, these regions on the opposing sides of the crossover point provide optimal spectral bands leading to unambiguous detection—namely a first optimal spectral band of about 2.05 to 2.15 µm (hereafter referred to as the l1=2.10 µm band) and another optimal spectral band of about 2.20 and 2.30 µm (hereafter referred to as the l2=2.25 µm band).

It should be understood that although the present teachings are directed to the measurement of radiance, measurements of reflectance can similarly be used at wavelengths shorter than about 3-4 µm. However, it should be noted that radiance measurements (instead of reflectance measurements) are simpler and typically sufficient for practical applications because typical targets of interest are illuminated with light sources containing relatively small or known power variations between 2.05 and 2.30 µm (e.g., clouds or surfaces illuminated by direct or indirect sunlight, or illuminated by a known light source). Therefore, the present teachings should not be regarded as being limited to only radiance measurements as reflectance and emittance measurements are also anticipated.

Figure 5:
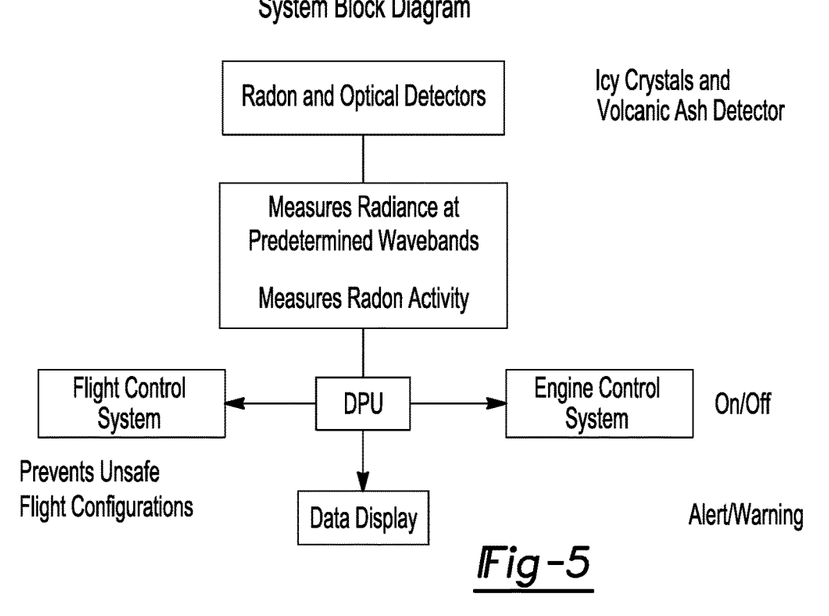
FIG. 5 is a block diagram of one possible embodiment of the ice crystals and volcanic ash hazardous detection system.

During operation, radon activity is measured continuously in air collected along the aircraft track, while ice crystals and volcanic ash are detected in the airspace immediately adjacent to the aircraft when in clouds and if desired ahead of an aircraft when the aircraft is flying outside clouds. To this end, as will be discussed herein, the hazardous detection system (FIGS. 5 and 6) can comprise an air sample collector probe 1, a radon activity measurement chamber 2, an optical detector 3 for making measurements of the radiance/emittance or reflectance in the aforementioned two spectral bands illustrated in FIGS. 3A, 3B and 4. In some embodiments, the detector 3 can be forward-looking, rearward-looking, or directed in another direction, as desired. In some embodiments, an in-situ sensor for making measurements of the outside temperature can further be used. Algorithms are provided for detecting ice crystals and volcanic ash in large concentrations in FIGS. 7 and 8.

During night operations, clouds in the airspace immediately around the aircraft can be illuminated with light sources containing the desired spectrum (FIGS. 3A and 3B). In some embodiments, light sources can be used to illuminate the airspace around the aircraft while the radiance or reflectance can be measured via detector 3. This detector can also be used to measure emittance in the spectral bands required for detecting volcanic ash (FIG. 4). In more complex embodiments, clouds in the airspace miles ahead of the aircraft can be illuminated with laser beams containing the desired spectrum. However, such complexity may not be required in most applications as simpler embodiments of the present teachings can be used to detect icing and volcanic ash hazards before problems occur and therefore the aircraft can be maneuvered safely away from hazardous areas.

System Description

In some embodiments, as referenced herein, radon activity detector chamber 2 can contain an alpha particle detector, or indirect methods capable of measuring the effects of ions produced by radon activity such as increases the conductivity of the air.

In addition, in some embodiments, light source 4 can comprise any source that is capable of outputting electromagnetic radiation within a predetermined light spectrum band. As described herein, it is desired to perform detection at an electromagnetic spectrum band, or a combination of spectrum bands around a crossover point. In particular, in some embodiments, light source 4 can output light at a single spectral band covering the range of interest such as the ideal band ranging from about 2.05 µm to about 2.30 µm. However, in some embodiments, light source 4 can output light covering two or more spectral bands, such as about 2.05 µm to about 2.15 µm and a second spectral band from about 2.15 µm to about 2.30 µm (or about 2.20 µm to about 2.30 µm).

Still further, in some embodiments, light source 4 can comprise any light source capable of outputting light in the spectral bands around crossover points such as for example in the SWIR spectrum, including lasers, halogen lights, infrared lights, light-emitting diodes, and the like. It should also be understood that alternative light sources can be used, such as naturally occurring light sources (e.g. sunlight, etc.). Therefore, it should be recognized that in some embodiments the present teachings do not require a supplied or otherwise powered light source, but may rely on sunlight or other naturally occurring or separately provided light sources.

In some embodiments, detector 3 can comprise any suitable detector or camera/imaging system capable of detecting and/or monitoring radiance and/or reflectance at spectral bands around crossover points. It should be understood that in some embodiments, detector 3 can be based on Indium Gallium Arsenide (InGaAs) technology, or can include or employ photodetectors, photodiodes, pyroelectric detectors, thermopile detectors, photoconductors, and other sensors, detectors, or camera, including RGB cameras. In some embodiments, detector 3 can comprise a single detector, camera, or other device for measuring radiance and/or reflectance. However, in some embodiments, detector 3 can comprise two or more detectors, cameras, or other devices that are each suitable for measuring radiance and/or reflectance for a specific spectrum range that is narrower than the total spectrum range of interest. In other words, a first detector can be used to detect radiance and/or reflectance in connection with spectrum in the left of a crossover point while a second detector can be used to detect radiance and/or reflectance in connection with spectrum in the right of a crossover point. This arrangement can permit monitoring and/or detection to occur simultaneously when used with a light source 4 that outputs the spectral range of interest. In some embodiments, detector 3 can comprise one or more cameras or detectors having a filter system that employs a plurality of filters to limit the detection of received wavelengths to a predetermined spectral band. In other embodiments the detectors sensitive to the spectral bands of interest can be used eliminating the need for filters. For example, a filter can be used to allow light in a spectral band from about 2.05 μm to about 2.15 μm to be detected while a second filter can be used to allow light in a spectral band from about 2.20 μm to about 2.30 μm range to be detected. Irrespective of the method of measuring and/or monitoring the reflected/received light, detector 3 outputs a detector signal representative to the measured radiance/reflectance.

In some embodiments, data processing unit 6 can comprise any suitable processing unit capable of determining a ratio of radiance measured at the first spectral band and at the second spectral band in response to the detector signal. Data processing unit 6 can comprise a central processing unit (CPU), in some embodiments, or may further simply be implemented through hardware design. Data processing unit 6 can further implement the algorithms described herein and output an output signal.

Finally, the output signal can be received by output device 7 and, in some embodiments, further processed in connection with other aircraft systems, such as alert displays, deicing or anti-icing equipment, or other systems or warnings.

Figure 7:
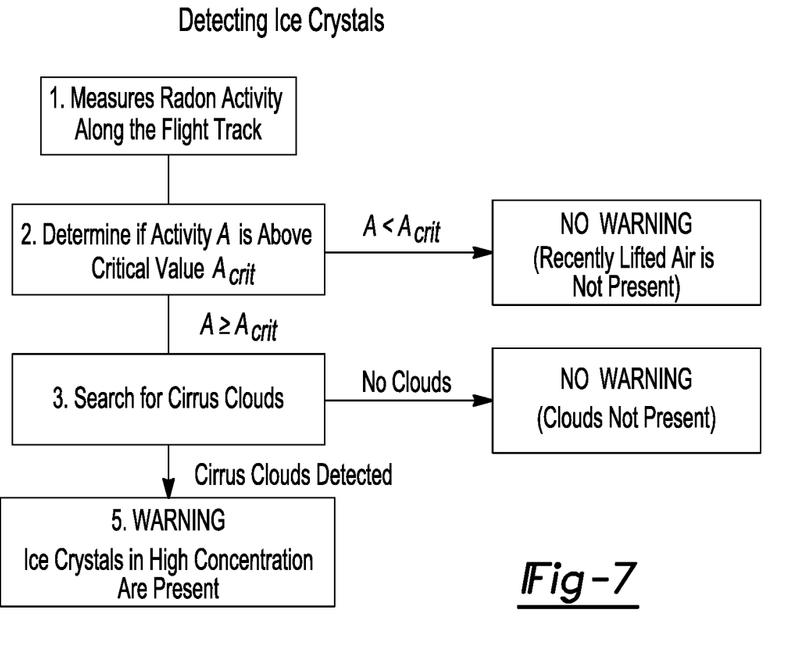
FIG. 7 is block diagram of the algorithm for the detection of ice crystals in large concentration.
Figure 8:
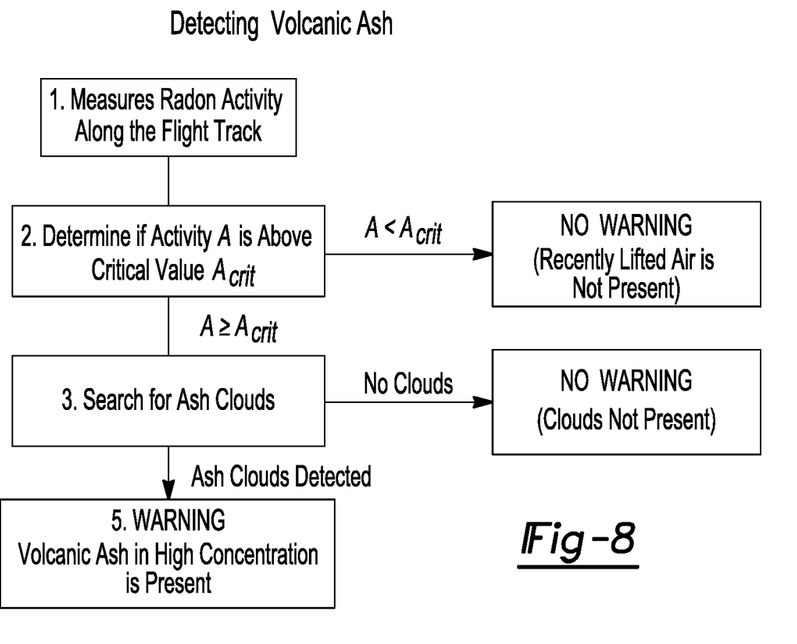
FIG. 8 is a block diagram of the algorithm for the detection of volcanic ash.

With particular reference to FIGS. 7 and 8, ice crystals and volcanic ash detection system is illustrated in accordance with some embodiments of the present teachings.

It should be understood that the probe 1 and detector 3 can be mounted anywhere on the aircraft, including the nose cone of an aircraft. Detector 3 can be mounted external or internal to the aircraft. However, it should be recognized that any protective coverings or windows 5 placed in front of detector 3 must permit transmission of the radiance spectrum of interest (e.g. must be transparent to shortwave infrared). Temperature sensors, thermostats, and/or heaters can be used with the coverings or windows to ensure proper transmission.

Methods

Figure 1:
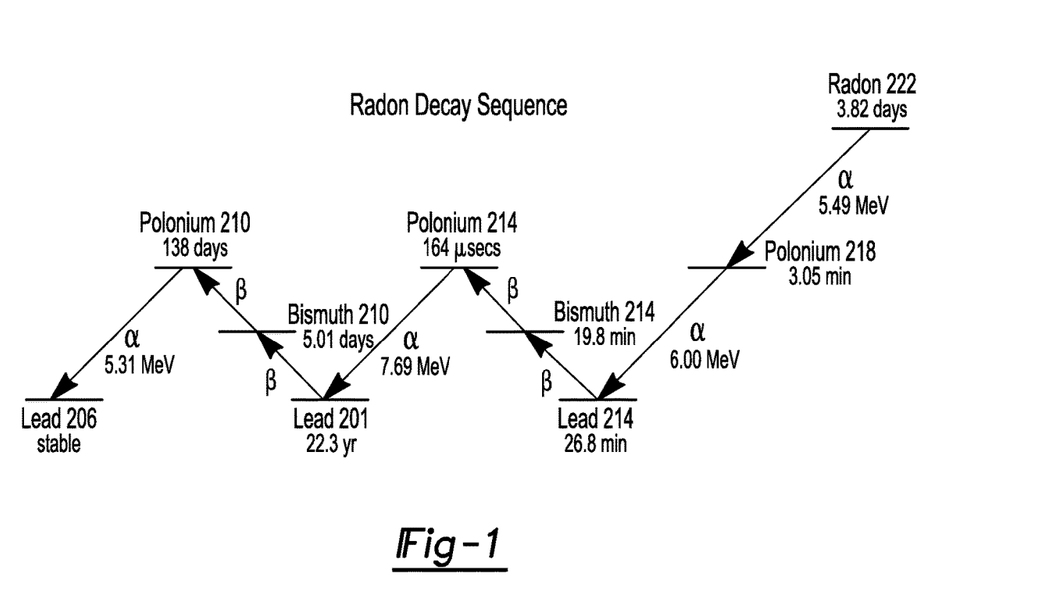
FIG. 1 is a sketch of the radon (radon-222) decay sequence indicating the decay products, their half-life time, and the particles emitted during the decay.
Figure 2:
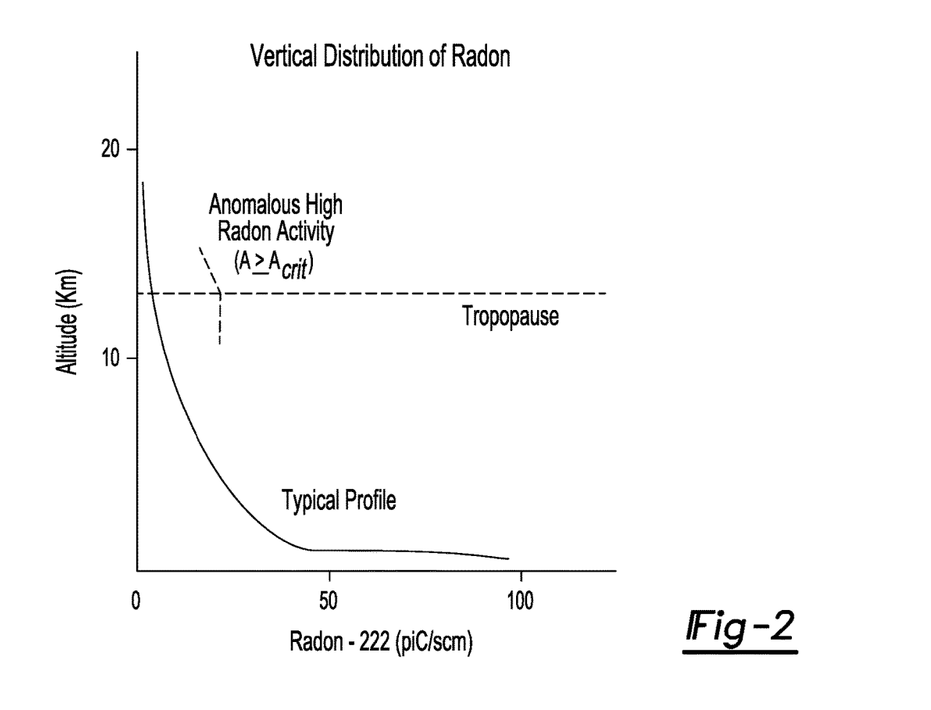
FIG. 2 is a sketch of the vertical distribution of radon in the atmosphere (radon-222) and the anomalous high values expected in areas containing volcanic ash and ice crystals in large concentrations.

According to some embodiments, as illustrated in FIGS. 5, 6, 7 and 8, the present teachings provide systems and methods for detecting ice crystals and volcanic ash in concentrations that are hazardous to aircrafts (e.g., airplanes, helicopters, blimps, UAVs). The present teachings provide a system for detecting these hazards in the airspace around aircrafts by detecting the presence of ice crystals or volcanic ash in air recently lifted from the lower troposphere to the aircraft's flight level. As discussed herein, the present teachings use measurements of radon activity to detect air recently transported from the lower troposphere to the aircrafts flight level as indicated in FIG. 2. Moreover, the present teachings use radiance, emittance or reflectance in the two spectral bands as indicated in FIGS. 3A, 3B and 4 to estimate the presence of ice crystals or volcanic ash in the airspace ahead of aircraft. The present teachings provide a system that alerts a human pilot or an autopilot to ice crystals or volcanic ash hazards when they are detected in the airspace immediately ahead of the aircraft.

It should be understood that the methods outlined herein are not limited to the exact order in which they are described because, in many cases, the specific order of operation may not be important.

An algorithm for detecting ice crystals in hazardous concentration is described in FIG. 7. It comprises of the following steps:

1. Radon activity A is measured along the flight track.
2. The radon activity measured along the flight track A is compared with the critical value $A_{crit}$ for the flight altitude (based on lookup tables or analytical expressions). If the measured value is below the critical value $A<A_{crit}$, no warning is issued. In this case, the algorithm returns to step 1.
3. If the radon activity measured along the flight track is equal or above the critical value $A \geq A_{crit}$, a search for ice crystals is conducted.
4. Multispectral measurements of the radiance of the area ahead of the aircraft at a spectral band on the left of a crossover point ($R_{l1}$), and at a spectral band on the right of the same crossover point ($R_{l2}$) are conducted. The ratio of the two values $\gamma = R_{l1}/R_{l2}$ are them compared to that of a pre-established critical value $\gamma_{crit}$.
5. If radon activity is equal or above the critical value $A \geq A_{crit}$, but ice crystals are not detected at the flight level $\gamma < \gamma_{crit}$, a "Ice Crystals in High Concentration" WARNING is NOT issued. However, in this case a CAUTION that updraft air was found at the flight level could be issued.
6. If radon activity is equal or above the critical value $A \geq A_{crit}$, and ice crystals are detected at the flight level $\gamma \geq \gamma_{crit}$, an "Ice Crystals in High Concentration" WARNING is issued.
7. Safety systems can be activated when warnings or cautions are issued, if desirable.

The present teachings also provide a system for detecting volcanic ash. An algorithm for detecting volcanic ash in hazardous concentration is described in FIG. 8. It comprises of the following steps:

1. Radon activity A is measured along the flight track.
2. The radon activity measured along the flight track A is compared with the critical value $A_{crit}$ for the flight altitude (based on lookup tables or analytical expressions). If the measured value is below the critical value $A<A_{crit}$, no warning is issued. In this case, the algorithm returns to step 1.

3. If the radon activity measured along the flight track is equal or above the critical value $A \geq A_{crit}$, a search for volcanic ash is conducted.

4. Multispectral measurements of the radiance/emittance of the area ahead of the aircraft at a spectral band on the left of the $\approx 8$ μm crossover point ($R_{\lambda 1} \approx 7-8$ μm), and at a spectral band on the right of the same crossover point ($R_{\lambda 2} \approx 8-10$ μm) are conducted. The ratio of the two values $\gamma = R_{\lambda 1}/R_{\lambda 2}$ are them compared to that of a pre-established critical value $\gamma_{crit}$.

5. If radon activity is equal or above the critical value $A \geq A_{crit}$, but volcanic ash is not detected at the flight level $\gamma < \gamma_{crit}$, a "Volcanic Ash in High Concentration" WARNING is NOT issued. However, in this case a CAUTION that updraft air was found at the flight level could be issued.

6. If radon activity is equal or above the critical value $A \geq A_{crit}$, and volcanic ash is detected at the flight level $\gamma \geq \gamma_{crit}$, an "Volcanic Ash in High Concentration" WARNING is issued.

7. Safety systems can be activated when either warnings or cautions are issued if desirable.

It should be understood that although certain features are described in connection with a particular application (e.g. airplane), this should not be regarded as limiting such certain features to only the particular application, as such certain features may be equally applicable to alternative applications (e.g. balloon).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways.

Such variations are not to be regarded as a departure from the disclosure, and all such modifications are intended to be included within the scope of the disclosure.

What is claimed is:

1. A system for detecting ice crystals and/or volcanic ash in an airspace of interest along a flight path of an airborne vehicle, the system comprising:
    a probe configured to collect an air sample in the airspace of interest;
    a radon detection system having a radon activity sensor measuring radon activity in the air sample and outputting a radon activity signal;
    a processing unit configured to determine if the radon activity is above a predetermined critical radon value for the airspace of interest, the predetermined critical radon value being greater than a non-convective background level for the airspace of interest, the processing unit configured to compare the radon activity signal to the predetermined critical value and output a radon determination signal indicative of recent convective updraft from lower troposphere;
    a spectral detection system configured to determine if ice crystals and/or volcanic ash are present in the airspace of interest when the radon activity is above the predetermined critical radon value and output an ice/ash detection signal, the spectral detection system having an optical sensor configured to measure radiance, emittance, and/or reflectance at spectral bands of interest on opposing sides of at least one crossover point in the airspace of interest; and
    the processing unit configured to determine a ratio of the measured radiance, emittance, and/or reflectance at the spectral bands and if the ratio is above a predetermined critical ratio value output an ice/ash determination signal indicative of the presence of ice crystals and/or volcanic ash in the airspace of interest.

2. The system according to claim 1, further comprising:
    a data display system displaying an indicia in response to the determination signal.

3. The system according to claim 1, further comprising:
    a system of an aircraft configured to be responsive to the determination signal.

4. The system according to claim 1, further comprising:
    a flight control system of an aircraft configured to be responsive to the determination signal.

5. The system according to claim 1, further comprising:
    a light source outputting light energy at the spectral bands of interest, the light source illuminating the area of interest.

6. The system according to claim 5 wherein the spectral bands of interest are in the range of about 2.05 μm to about 2.30 μm.

7. The system according to claim 5 wherein the light source is selected from the group consisting of a laser, halogen light, infrared light, and light-emitting diode.

8. A method for detecting ice crystals and/or volcanic ash in an airspace of interest along a flight path of an airborne vehicle, the method comprising:
    measuring radon activity A in an airspace in which an aircraft is flying;
    determining if the radon activity A is above a predetermined critical radon value $A_{crit}$ for the airspace of interest, the predetermined critical radon value being greater than a non-convective background level for the airspace of interest,
    if the radon activity A is above the predetermined critical radon value ($A \geq A_{crit}$) then producing a radon determination signal indicative of recent convective updraft from lower troposphere has been detected,
    if the radon activity A is above the predetermined critical radon value ($A \geq A_{crit}$) then measuring radiance, emittance, and/or reflectance at spectral bands of interest on opposing sides of at least one crossover point in the airspace of interest and determining a ratio of the measured radiance, emittance, and/or reflectance at the spectral bands, and
    if the ratio above a predetermined critical ratio value then output an ice/ash determination signal indicative of the presence of ice crystals and/or volcanic ash in the airspace of interest.

9. The method according to claim 8, wherein the measuring radiance, emittance, and/or reflectance at spectral bands of interest on opposing sides of at least one crossover point in the airspace of interest and determining a ratio of the measured radiance, emittance, and/or reflectance at the spectral bands comprises:
    measuring a first radiance of the airspace of interest at a first spectral band on a first side of the crossover point ($R_{\lambda 1}$);
    measuring a second radiance of the airspace of interest at a second spectral band on a second opposing side of the crossover point ($R_{\lambda 2}$); and calculating the ratio of the first radiance and the second radiance ($\gamma = R_{\lambda,1}/R_{\lambda,2}$.

* * * * *

UNITED STATES PATENT AND TRADEMARK OFFICE
CERTIFICATE OF CORRECTION

PATENT NO. : 10,336,465 B2
APPLICATION NO. : 15/399088
DATED : July 2, 2019
INVENTOR(S) : Rennó

Page 1 of 1

It is certified that error appears in the above-identified patent and that said Letters Patent is hereby corrected as shown below:

In the Claims

Column 13, Claim 9, Line 2, delete "$(\gamma=R_{\lambda 1}/R_{\lambda 2}.$" and insert -- $(\gamma=R_{\lambda 1}/R_{\lambda 2})$. -- therefor Signed and Sealed this
Eleventh Day of February, 2020

Andrei Iancu
*Director of the United States Patent and Trademark Office*